(12) United States Patent
Bowe et al.

(10) Patent No.: US 6,771,996 B2
(45) Date of Patent: Aug. 3, 2004

(54) ABLATION AND HIGH-RESOLUTION MAPPING CATHETER SYSTEM FOR PULMONARY VEIN FOCI ELIMINATION

(75) Inventors: Wade A. Bowe, Temecula, CA (US); Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/866,049

(22) Filed: May 24, 2001

(65) Prior Publication Data

US 2002/0177765 A1 Nov. 28, 2002

(51) Int. Cl.[7] ............................. A61B 5/04; A61B 18/14
(52) U.S. Cl. ......................... 600/374; 600/381; 606/41
(58) Field of Search ............................. 606/39, 38, 41, 606/46, 47, 48–50; 607/101–102, 122, 123; 604/528; 600/374, 381

(56) References Cited

U.S. PATENT DOCUMENTS

| | | | | |
|---|---|---|---|---|
| 4,458,677 A | * | 7/1984 | McCorkle, Jr. ............. | 607/123 |
| 5,100,423 A | | 3/1992 | Fearnot | |
| 5,549,109 A | * | 8/1996 | Samson et al. ............. | 607/122 |
| 5,681,280 A | | 10/1997 | Rusk | |
| 5,755,760 A | | 5/1998 | Maguire et al. | |
| 5,807,324 A | * | 9/1998 | Griffin, III ................ | 607/116 |
| 5,928,163 A | | 7/1999 | Roberts et al. | |
| 5,971,983 A | | 10/1999 | Lesh | |
| 6,012,457 A | | 1/2000 | Lesh | |
| 6,024,740 A | | 2/2000 | Lesh | |
| 6,041,260 A | | 3/2000 | Stern et al. | |
| 6,071,279 A | | 6/2000 | Whayne et al. | |
| 6,088,610 A | * | 7/2000 | Littmann et al. .......... | 600/381 |
| 6,117,101 A | | 9/2000 | Diederich et al. | |
| 6,161,543 A | | 12/2000 | Cox et al. | |
| 6,164,283 A | | 12/2000 | Lesh | |
| 6,214,002 B1 | | 4/2001 | Fleischman et al. | |
| 6,314,963 B1 | * | 11/2001 | Vaska et al. ................ | 606/41 |
| 6,315,778 B1 | * | 11/2001 | Gambale et al. ............ | 606/41 |
| 6,325,797 B1 | * | 12/2001 | Stewart et al. .............. | 606/41 |
| 6,385,472 B1 | * | 5/2002 | Hall et al. .................. | 607/122 |
| 6,529,756 B1 | * | 3/2003 | Phan et al. ................ | 600/374 |
| 6,652,517 B1 | * | 11/2003 | Hall et al. .................. | 606/41 |

OTHER PUBLICATIONS

Mudit K. Jain, B.E., Gery Thomassoni, M.D., Richard E. Riley, M.S., and Patrick D. Wolf, Ph.D., "Effect of Skin Electrode Location on Radiofrequency Albation lesions: An In Vivo and a Three–Dimensional Finite Element Study," Journal of Cardiovascular Electrophysiology, vol. 9, #12, Dec. 1998, pp. 1325–1335; Futura Publishing Company, Inc., Armonk, NY.

* cited by examiner

Primary Examiner—Lee Cohen
(74) Attorney, Agent, or Firm—Fulwider Patton Lee & Utecht, LLP (57) ABSTRACT

A catheter system includes an outer catheter having a lumen and an inner catheter sized to fit within and slide through the lumen of the outer catheter. Both catheters may be introduced into an anatomical site through a single introduction path. At the distal-end region of each catheter is an electrode system. One electrode system is for mapping the site; the other is for ablating the site. The distal-end regions of one or both of the catheters may be linear shaped, circular shaped, or radially expandable. When the catheter system is deployed the electrode systems carried by the distal-end regions of the mapping catheter and the ablation catheter are movable relative to each other and tend to lie in planes substantially parallel to each other. Another catheter system includes two separate electrode systems on a single expandable member shaped so that both electrode systems come in contact with separate sites.

29 Claims, 9 Drawing Sheets

ABLATION AND HIGH-RESOLUTION MAPPING CATHETER SYSTEM FOR PULMONARY VEIN FOCI ELIMINATION

BACKGROUND OF THE INVENTION

The invention relates generally to an electrophysiological ("EP") catheter system for use on biological tissue within a biological site, and more particularly, to a combined mapping and ablating catheter system for use in and around the pulmonary veins.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

Cardiac arrhythmia, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmia may also have a focal origin, such as when an isolated region of tissue in an atrium fires autonomously in a rapid, repetitive fashion.

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium.

One such EP catheter system, as disclosed in U.S. Pat. Nos. 6,059,778 and 6,096,036, includes a plurality of spaced apart band electrodes located at the distal-end of the catheter and arranged in a linear array. The band electrodes are positioned proximal heart tissue. RF energy is applied through the electrodes to the heart tissue to produce a series of long linear lesions similar to those produced by the Maze procedure.

As previously mentioned, cardiac arrhythmia, such as atrial fibrillation, may be focal in nature. The foci, defined by regions exhibiting a consistent and centifugal pattern of electrical activation, may act as either a trigger of atrial fibrillation paroxysmal or may even sustain fibrillation. Such focal arrhythmia are known to originate from a tissue region along the pulmonary veins of the left atrium, and more particularly in the superior pulmonary veins.

Procedures for the treatment of focal arrhythmia involving the pulmonary vein generally require the use of two separate catheter systems—a mapping catheter system for locating the foci and an ablation catheter system for ablating the foci. Both catheter systems include their respective mapping or ablation catheter and either a guiding catheter or a guide wire for introducing the catheter into the left atrium of the heart. During a typical procedure, the mapping catheter is first introduced into the left atrium through a puncture in the septum between the right and left atria. The mapping catheter is then guided into the pulmonary vein. While the mapping catheter is still within the heart, the ablation catheter is introduced into the left atrium through either the same puncture as the mapping catheter or a separate puncture. Using the mapping catheter, the foci of the arrhythmia is located using any of several well known mapping techniques. After it is determined that the foci are located within the pulmonary vein, the ablation catheter is positioned either in the pulmonary vein or around the pulmonary vein ostium and the tissue is ablated. The procedure thus described requires the simultaneous placement of two separate catheters into the left atrium through either one or two separate introduction paths. In the case of the left atrium such introduction paths comprise punctures through the atrial septum between the right and left atria. Passing two catheters through a single puncture or two separate punctures increases patient trauma. It also increases the likelihood of damaging the heart through tearing of the septum.

Hence, those skilled in the art have recognized a need for a catheter system having two independent catheters, each capable of being introduced into the heart via a single transseptal introduction path. The need for a combined mapping and ablation catheter system for use in the pulmonary vein has also been recognized. The invention fulfills these needs and others.

SUMMARY OF THE INVENTION

Briefly, and in general terms, the invention is directed to a combination mapping and ablating catheter system for use during electrophysiological procedures in and around various biological sites, including the pulmonary veins.

In a first aspect, the invention relates to a catheter system that includes an outer catheter having a lumen therethrough and a distal-end region carrying a first electrode system. The catheter system also includes an inner catheter that is sized to fit within and slide through the lumen of the outer catheter. The inner catheter has a distal-end region carrying a second electrode system.

By providing an outer catheter having a lumen through which a separate inner catheter may slide, the invention allows for the simultaneous placement of two separate catheters into a biological site through a signal introduction path. As such, the likelihood of damaging the biological site is substantially reduced.

In detailed aspects of the invention, either one or both of the outer catheter and inner catheter further include a tendon having a distal end attached to the distal-end region of the respective catheter and a proximal end exiting the proximal end of the catheter. The tendon is attached such that movement of the tendon along the length of the catheter causes the distal-end region of that catheter to curve. In a another detailed aspect, the outer catheter further comprises a shaped-memory stylet for imparting a preshaped curve to the distal-end region of the outer catheter. In a further detailed aspect, the preshaped curve has a radius of curvature and the catheter further comprises a tendon having a distal end attached to the distal end of the catheter and a proximal end exiting the proximal end of the catheter. The tendon is attached such that movement of the tendon along the length of the catheter decreases the radius of curvature.

In another detailed facet of the invention, the outer catheter includes an outer tubular member and an inner tubular member slidably disposed within the outer tubular member. The inner tubular member defines the lumen of the outer catheter. The other catheter also includes a plurality of outwardly bendable segments. The segments are secured at their distal ends to the distal-end region of the inner tubular member and at their proximal ends to the outer tubular member at a point proximal the attachment points of the distal ends. Movement of the inner tubular member in the proximal direction relative the outer tubular member causes the segments to bend outward.

In another aspect, the invention relates to a catheter system that includes an outer catheter having tubular wall defining a lumen. The tubular wall includes a sidewall orifice. The outer catheter also includes a distal-end region carrying a first electrode system and a proximal-end region. The catheter system further includes an inner catheter sized to fit within the lumen of the outer catheter and to slide therein. The inner catheter is also sized to fit through the sidewall orifice. The inner catheter has a distal-end region carrying a second electrode system.

In a detailed facet of the invention, the tubular member comprises a resiliently deformable junction section between the distal-end region and the proximal end region. The junction section has a normally bent form that generally aligns the center of the sidewall orifice with the axis of the proximal-end region of the tubular wall. In another detailed aspect, the outer catheter further includes a tendon having a distal end attached proximate the inner wall of the tubular member and a proximal end exiting the proximal end of the tubular member. Movement of the tendon along the length of the tubular member causes the distal-end region to deflect about the junction section relative to the proximal-end region. In yet another detailed aspect, the outer catheter includes a shaped-memory stylet for imparting a generally circular curve to the distal-end region of the tubular wall. The curve lies substantially within a first plane. The inner catheter also includes a shaped-memory stylet for imparting a generally circular curve to the distal-end region of the inner catheter. This curve lies substantially within a second plane that is substantially parallel to the first plane.

In another detailed facet of the invention the first electrode system and the second electrode system each comprise a plurality of band electrodes positioned along the length of the their respective distal-end region. The catheter system further comprises an alignment system that is adapted to align the curved distal-end region of the inner catheter with the curved distal-end region of the outer catheter such that the band electrodes of the respective catheters are aligned with each other. In a further detailed aspect, the alignment system comprises a pair of markers, each visible under fluoroscopy. One marker is carried on the proximal region of the inner catheter while the other marker is carried on the proximal region of the outer catheter.

In another further detailed aspect, the alignment system comprises a groove along the outer surface of the proximal region of the inner catheter and a complementary protrusion along the inner surface of the outer catheter.

In another facet, the invention relates to a method of performing an electrophysiological procedure on biological tissue within a biological site. The method includes positioning a first catheter, having a distal-end region carrying a first electrode system, within the biological site proximate the biological tissue. The method further includes sensing electrical activity within the tissue through the first electrode system and processing the electrical activity to identify the origin of an electrophysiological condition. The method further includes guiding a second catheter, having a distal-end region carrying a second electrode system, via the first catheter, into the biological site. The method also includes positioning the second catheter such that the second electrode system is adjacent the identified origin and applying energy to the second electrode system to ablate the identified origin.

In a detailed aspect of the invention, the first catheter includes a tubular wall defining a lumen and guiding the second catheter includes sliding the second catheter through the lumen. In a further detailed facet, positioning the second catheter such that the second electrode system is adjacent the identified source includes sliding the second catheter through the lumen until the second electrode system is substantially coincident with the first electrode system and repositioning the first catheter relative the second catheter to expose the second electrode system. In another detailed aspect, the second catheter includes a tubular wall defining a lumen and guiding the second catheter includes sliding the second catheter over the first catheter. In a further detailed aspect, positioning the second catheter such that the second electrode system is adjacent the identified source includes sliding the second catheter over the first catheter until the second electrode system is coincident with the first electrode system.

In another facet, the invention relates to a method of performing an electrophysiological procedure on biological tissue proximate a pulmonary vein. The method includes positioning a first catheter, having a distal-end region carrying a first electrode system, near the ostium of the pulmonary vein and guiding a second catheter, via the first catheter, into the pulmonary vein. The second catheter has a distal-end region carrying a second electrode system. The method further includes sensing electrical activity within the pulmonary-vein tissue through the first electrode system, processing the electrical activity to confirm the existence of an abnormal electrophysiological condition originating within the pulmonary vein and upon confirmation, applying energy to the first electrode system to ablate the tissue near the ostium.

In a detailed facet of the invention, the first catheter further includes a resiliently deformable shaped-memory stylet for imparting a generally circular curve to the distal-end region of the first catheter and positioning the first catheter near the ostium of the pulmonary vein includes the steps of straightening the distal-end region to allow entry of the distal-end region into the heart, allowing the distal-end region to assume its curved shape and positioning the distal-end region at the ostium such that the curved portion of the region contacts the tissue defining the ostium. In another detailed aspect, the second catheter further includes a resiliently deformable shaped-memory stylet for imparting a generally circular curve to the distal-end region of the second catheter and positioning the second catheter within the pulmonary vein includes the steps of straightening the distal-end region to allow entry of the distal-end region into the pulmonary vein, allowing the distal-end region to assume its curved shape and positioning the distal-end region within the vein such that the curved portion of the region contacts the tissue defining the vein lumen.

In another aspect, the invention relates to a catheter system including a catheter sheath carrying a circumferentially expandable member at its distal end. The catheter system further includes a first electrode system positioned on the expandable member and a second electrode system positioned on the expandable member, proximal the first electrode system.

In a detailed aspect of the invention, the expandable member includes a distal segment with a first expandable diameter and a proximal segment with a second expandable diameter greater than the first expandable diameter. The first electrode system is positioned at the distal segment and the second electrode system positioned at the proximal segment. In further detailed aspects either one or both of the first electrode system and second electrode system includes a plurality of electrode elements arranged to form a circumferential band around the expandable member.

In another aspect, the invention relates to a method of performing an electrophysiological procedure on biological tissue proximate a pulmonary vein. The method includes positioning a circumferentially expandable member having a distal-end region with a first electrode system and a proximal-end region with a second electrode system in the heart such that the distal-end region is at least partially within the pulmonary vein and the proximal-end region is adjacent the tissue defining the ostium of the pulmonary vein. The method also includes expanding the circumferentially expandable member such that the first electrode system contacts the tissue defining the pulmonary vein and the second electrode system contacts the tissue defining the ostium, sensing electrical activity within the pulmonary-vein tissue through the first electrode system and processing the electrical activity to confirm the existence of an abnormal electrophysiological condition originating within the pulmonary vein. The method further includes applying energy to the first electrode system to ablate the tissue near the ostium upon confirmation of the existence of an abnormal electrophysiological condition.

These and other aspects and advantages of the invention will become apparent from the following detailed description and the accompanying drawings which illustrate by way of example the features of the invention.

BRIEF DESCRIPTION OF THE DRAWINGS

FIGS. 9A and 9B are side views of the ablation catheter of FIG. 9A showing the normally curved distal end region deflected by the steering mechanism such that the distal-end region lies in a plane at an angle relative to the axis of the proximal-end region of the catheter.

DETAILED DESCRIPTION OF THE PREFERRED EMBODIMENTS

Figure 1:
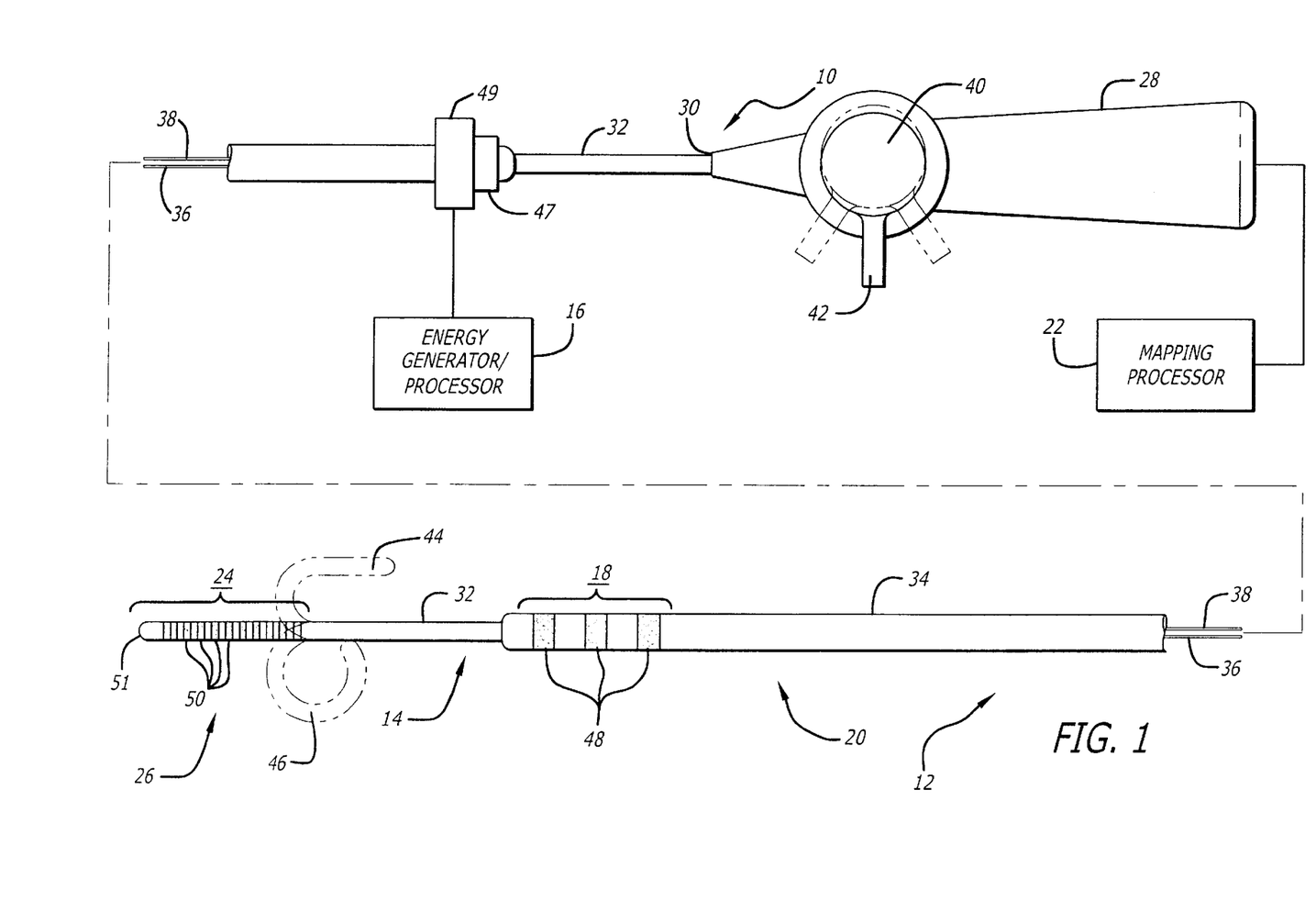
FIG. 1 depicts a catheter system configured in accordance with one embodiment of the invention including a mapping catheter slidably positioned within an open-lumen ablation catheter.

Turning now to the drawings, in which like reference numerals are used to designate like or corresponding elements among the several figures, in FIG. 1 there is shown a catheter system 10 including an outer ablation catheter 12 having a lumen throughout and an inner mapping catheter 14 configured to fit and slide within the lumen of the outer ablation catheter. The catheters 12, 14 may be of various sizes depending on the intended use of the catheter system 10. In one configuration of a catheter system intended for use within the heart, and particularly, the pulmonary vein, the outer ablation catheter has an outside diameter of 2.39 millimeters (0.094 inches) (7 French) and the inner mapping catheter has an outside diameter of 1.67 millimeters (0.0657 inches) (5 French).

Electrically connected to the outer ablation catheter 12 is an energy generator/processor 16. The energy generator/processor 16 is adapted to provide energy to an ablation electrode system 18 located at the distal-end region 20 of the outer ablation catheter 12 and to monitor the temperature at the ablation electrode system. Electrically connected to the inner mapping catheter 14 is a mapping processor 22 adapted to receive electrical signals from a mapping electrode system 24 located at the distal-end region 26 of the inner mapping catheter. Details regarding the ablation electrode system 18, the mapping electrode system 24 and their respective electrical connections are provided below.

With continued reference to FIG. 1, the inner mapping catheter 14 includes a catheter handle 28 attached to a proximal end 30 of a mapping catheter sheath 32. Housed within the mapping catheter sheath 32 are a first steering tendon 36 and a second steering tendon 38. The first steering tendon 36 and the second steering tendon 38 exit the proximal end of the catheter sheath 32 and enter the catheter handle 28. Within the catheter handle 28, the first 36 and second 38 steering tendons attach to a steering controller 40. The distal ends of the steering tendons 36, 38 are attached to a distal-end region 26 of the inner mapping catheter 14.

With further reference to FIG. 1, the profile of the distal-end region 26 of the mapping catheter sheath 32 can be adjusted by rotating the steering controller 40. The steering controller 40 can be rotated by rotating a knob 42 either clockwise or counterclockwise. Rotating the knob 42 clockwise from a neutral position causes one of the steering tendons 36, 38 to translate axially in the proximal direction, thus creating a first changed profile 44 of the distal-end region 26. Similarly, rotating the knob 42 counterclockwise from a neutral position causes the other steering tendon 36, 38 to translate axially in the proximal direction, thus creating a second changed profile 46 of the distal-end region 26. Although FIG. 1 depicts the handle 28 being used with a dual-profile catheter with two steering tendons 36, 38, the handle is also functional for single-profile catheters with a single steering tendon.

The ablation electrode system 18 includes one or more band electrodes 48 arranged in a linear array. In a preferred embodiment, the ablation electrode system 18 includes three, 3 millimeter wide band electrodes spaced 4 millimeters apart. A plurality of feed wires (not shown) extend through wire lumen (not shown) running the length of the ablation catheter sheath 34. The wires are electrically connected to the ablation electrodes 48 at their distal ends and to an electrical connector 49 at their proximal ends. The electrical connector 49 provides the interface between the energy generator/processor 16 and the lead wires. The lead wires transfer energy from the energy generator/processor 16 to the band electrodes 48. The lead wires may also provide temperature signals to the energy generator/processor 16.

The mapping electrode system 24 includes a plurality of band electrodes 50 and a tip electrode 51 arranged in a linear array. The band electrodes 50 are spaced close together for high resolution and in a preferred embodiment includes eight 1 millimeter wide band electrodes spaced 1 millimeter apart. A plurality of lead wires (not shown) extend through the mapping catheter sheath 32. The wires are electrically connected to the mapping electrodes 50, 51 at their distal ends and to an electrical connector (not shown) at the rear of the handle 28 at their proximal ends. The electrical connector provides the interface between the mapping processor 22 and the lead wires. The lead wires transfer electrical signals to the mapping processor.

To assist in steering the catheter system 10 through the patient's vascular system and to assure proper placement of the ablation electrode system 18, the distal-end region 26 of the mapping catheter sheath 32 is made more rigid than the distal-end region 20 of the ablation catheter sheath 34. This may be accomplished, for example, by forming the distal-end region 26 of the mapping catheter sheath 32 of a higher durometer than the distal-end region 20 of the ablation catheter sheath 34. As such, the distal-end region 20 of the outer ablation catheter 12 assumes the shape of the distal-end region 26 of the inner mapping catheter 14.

To prevent fluid from entering the space between the inside wall of the outer ablation catheter 12 and the outside surface of the inner mapping catheter 14, a seal (not shown) is included in the outer ablation catheter. The seal is a soft rubber short-length tubing or O-ring formed of an elastomeric material, e.g., silicon, Santoprene, Viton, and is adhered to the inside diameter of the outer ablation catheter 12 lumen near the distal end. The seal forms a tight seal against the outer surface of the inner mapping catheter 14. The seal is pliable enough to allow for movement of the outer ablation catheter 12 relative to the inner mapping catheter 14 yet rigid enough to function as a seal. The outer ablation catheter 12 also includes a locking mechanism 47 for locking the outer ablation catheter to the inner mapping catheter 14. An example of one such locking mechanism is described in U.S. application Ser. No. 09/746,721 the disclosure of which is hereby incorporated by reference.

While the operational descriptions to follow focus on the use of the catheter system 10 for treating focal arrthymias originating within and around the pulmonary vein, the system may be used for treatment of other locations both within and outside of the heart. For procedures not involving the pulmonary vein, the catheter system 10 may be initially placed within the subject biological site using the steering system of the inner mapping catheter 14. In such placement procedures, the outer ablation catheter 12 and the inner mapping catheter 14 are positioned relative each other such that their distal ends are substantially aligned. The catheters 12, 14 are then introduced into a patient's vascular system and are guided therethrough and into the desired biological site, using the mapping catheter's steering system. For procedures involving the pulmonary vein, the catheter system 10 may be initially placed within the left atrium through a transseptal approach using a guiding sheath (not shown). Once positioned, the guiding sheath and the catheter system 10 are moved relative to each other to expose the distal end regions 20, 26 of the catheter system 10.

Figure 2:
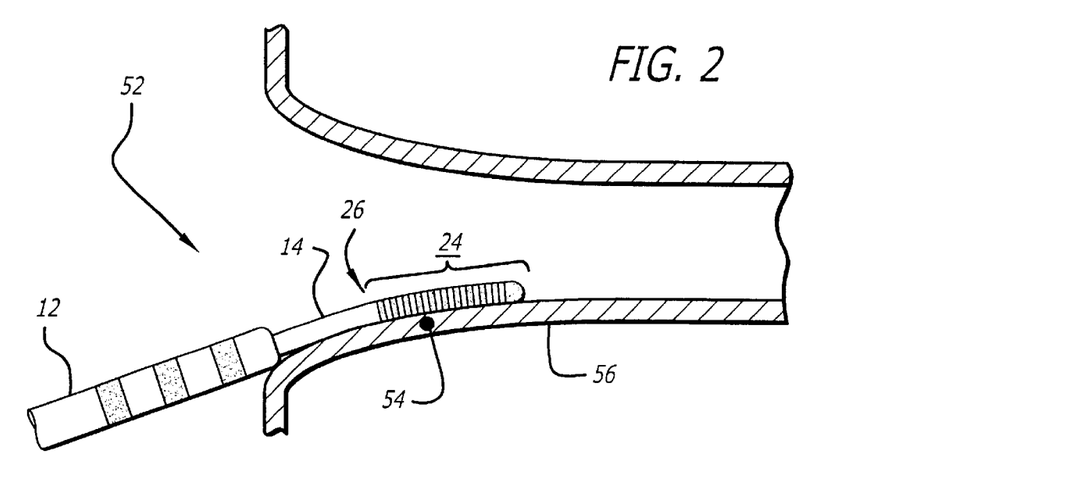
FIG. 2 depicts the catheter system of FIG. 1 positioned near the ostium of a vein with the ablation catheter retracted to exposed the mapping catheter such that the mapping catheter may locate the focal origin of an arrhythmia.

With reference to FIG. 2, once the outer ablation catheter 12 and the inner mapping catheter 14 are positioned in the left atrium near the pulmonary vein 52, the outer ablation catheter is retracted in the proximal direction relative to the inner mapping catheter to expose the distal-end region 26 of the inner mapping catheter. The distal-end region 26 is guided into the vein and is positioned against the tissue 56 defining the vein lumen. The profile of the distal-end region 26 of the inner mapping catheter 14 may be deflected using the steering system to ensure better contact between the mapping electrode system 24 and the tissue 56. Electrical signals traveling through the tissue 56 are sensed by the mapping electrode system 24 and are sent to the mapping processor 22 (FIG. 1) for analysis. The mapping electrode system 24 is repositioned and then the process is repeated until the foci 54 of the arrthymia are located.

Figure 3:
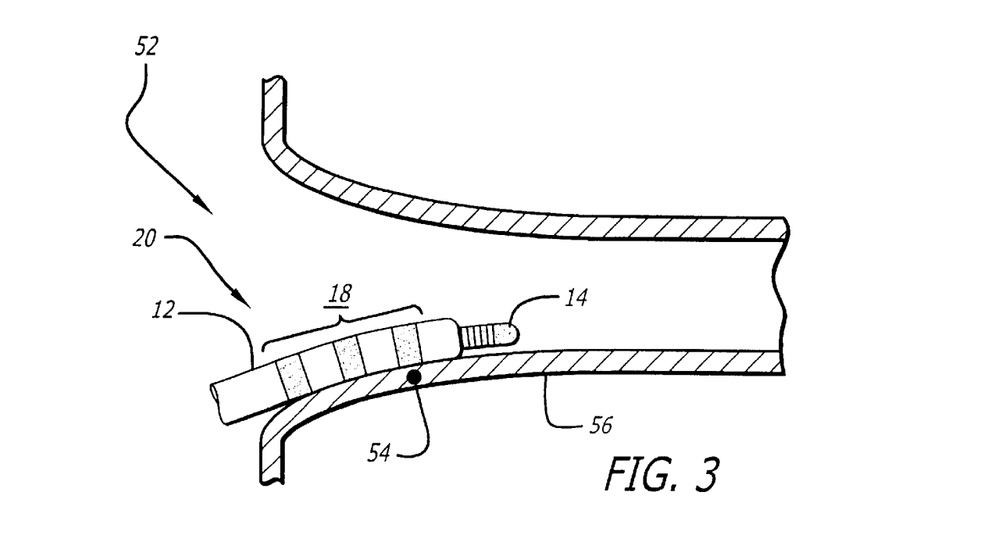
FIG. 3 depicts the catheter system of FIG. 2 positioned near the ostium of a vein with the ablation catheter advanced to coincide with the focal origin previously located by the mapping catheter.

With reference to FIG. 3, once the foci 54 are located, the outer ablation catheter 12 is advanced distally over the inner mapping catheter 14 until the ablation electrode system 18 is at or near the foci 54. Because the distal-end region 20 of the outer ablation catheter 14 is more pliable than the inner mapping catheter 12, it assumes the shape of the mapping catheter and is thus placed at or near the foci 54. In a preferred embodiment, markers (not shown) are placed on both the inner mapping catheter 14 and outer ablation catheter 12. Under fluoroscopy, the markers are used to align the ablation electrode system 18 with the mapping electrode system 24 and hence with the foci 54. Once properly positioned, energy is applied to the ablation electrode system 18 from the energy generator/processor 16 (FIG. 1). In a preferred embodiment the energy generator/processor 16 provides RF energy. In alternate embodiments, other forms of energy may be applied such as cyroablation, light, radiation, laser and any other energy capable of permanently disrupting the electrical continuity of the pulmonary vein 52. In the embodiment shown, the RF energy passes through the ablation electrode system 18 into the tissue 56 at or near the foci 54 to ablate the tissue.

Figure 4:
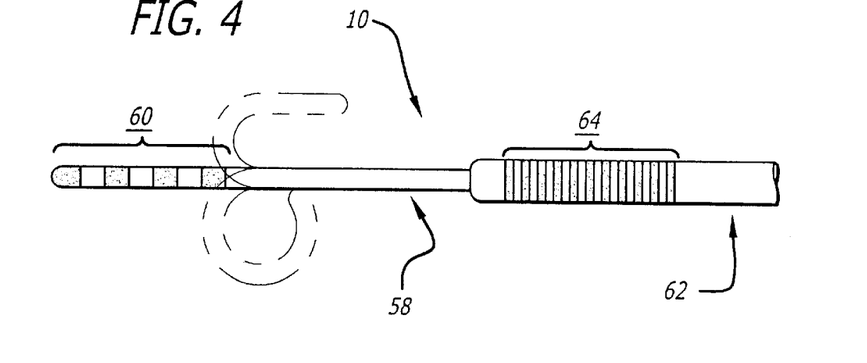
FIG. 4 depicts the distal-end region of an alternate configuration of the catheter of FIG. 1 wherein the ablation catheter is slidably positioned within an open-lumen mapping catheter.

With reference to FIG. 4, in an alternate configuration of this embodiment of the invention, the catheter system 10 includes an inner ablation catheter 58 having an ablation electrode system 60 and an outer mapping catheter 62 having a mapping electrode system 64. The inner ablation catheter 58 includes a steering mechanism like that described with reference to the inner mapping catheter 14 (FIG. 1) of the previous embodiment.

Figure 5:
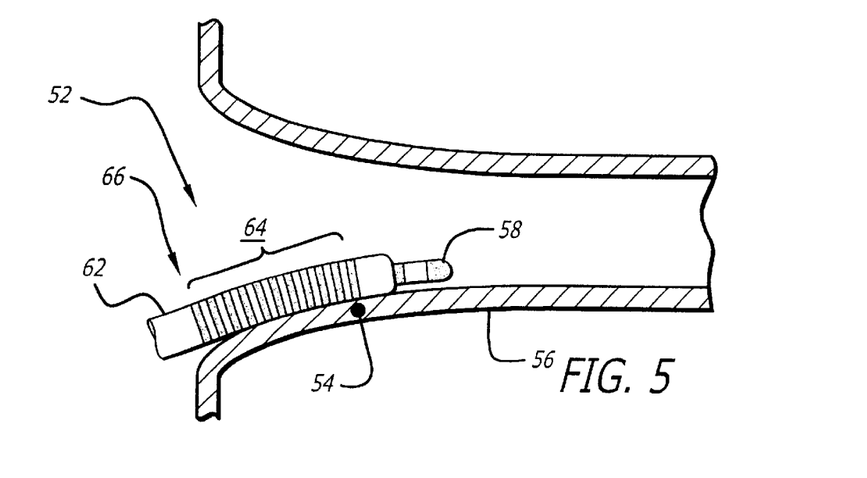
FIG. 5 depicts the catheter system of FIG. 4 positioned near the ostium of a vein with the mapping catheter advanced over the ablation catheter such that the mapping catheter may locate the focal origin of an arrhythmia.

In operation, as shown in FIG. 5, once the outer mapping catheter 62 and the inner ablation catheter 58 are positioned in the heart, the distal-end region 66 of the outer mapping catheter 62 is guided into the vein 52 and is positioned against the tissue 56 defining the vein lumen. Electrical signals traveling through the tissue 56 are sensed by the mapping electrode system 64 and are sent to the mapping processor 22 (FIG. 1) for analysis. The mapping electrode system 64 is repositioned and then the process is repeated until the foci 54 of the arrthymia are located.

Figure 6:
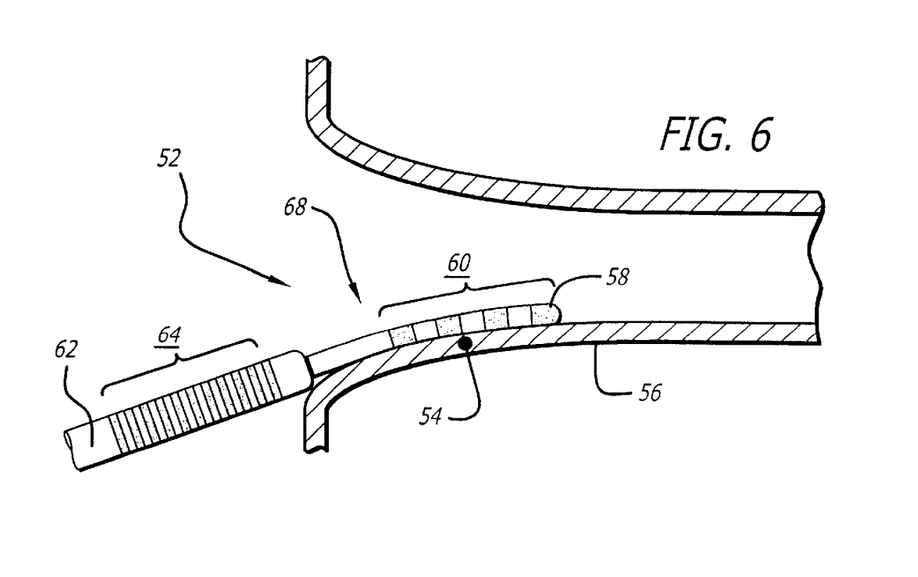
FIG. 6 depicts the catheter system of FIG. 5 positioned near the ostium of a vein with the mapping catheter retracted to allow the ablation catheter to coincide with the focal origin previously located by the mapping catheter.

With reference to FIG. 6, once the foci 54 are located, the outer mapping catheter 62 is retracted proximally relative to the inner ablation catheter 58 to expose the ablation electrode system 60 at or near the foci 54. The distal-end region 68 of the inner ablation catheter 58 is positioned such that it contacts the tissue 56 at or near the foci 54. The distal-end region 68 of the ablation catheter 58 may be deflected using the steering system to ensure adequate contact between the ablation electrode system 60 and the tissue 56. Once adequately positioned, energy is applied to the ablation electrode system 60 by the energy generator/processor 16 (FIG. 1) to ablate the tissue 56 at or near the foci 54.

In other embodiments of the invention the catheter system includes an ablation catheter that is specially configured to ablate a circumferential band of tissue near the entry of the pulmonary vein lumen. A "circumferential band" as used herein is a continuous line that is traced around a region of space and which starts and ends at substantially the same location. The catheter system also includes a mapping catheter that is also specially configured to circumscribe a band of tissue within the vein lumen.

Figure 7:
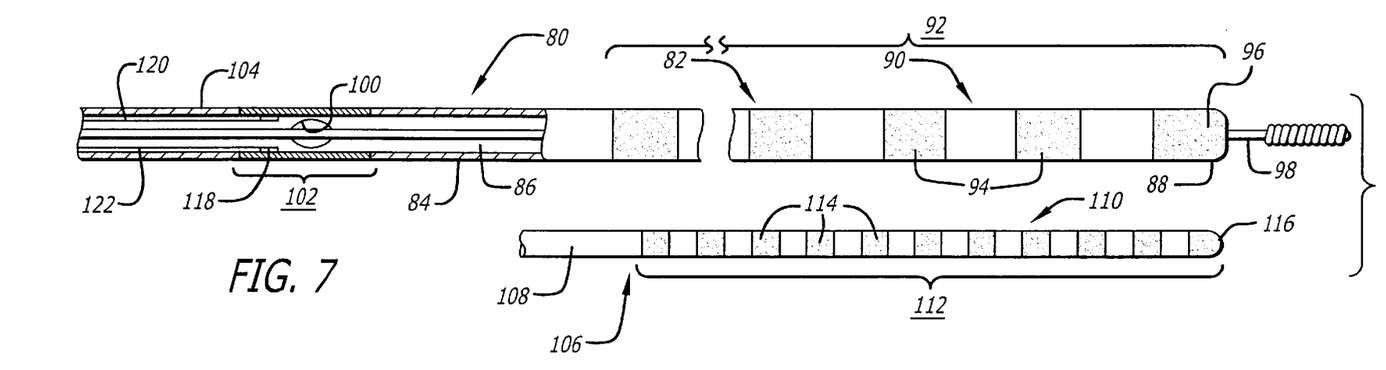
FIG. 7 is a side view with partial cutaway of a catheter system configured in accordance with another embodiment of the invention including an open-lumen ablation catheter having a precurved distal-end region (shown straightened by a guidewire), a steering system and a sidewall orifice and a mapping catheter sized to fit within the ablation catheter and having a normally curved distal-end region (shown straightened)

With reference to FIG. 7 one such catheter system 80 includes an outer ablation catheter 82 having a tubular wall 84 defining a lumen 86. The lumen 86 extends between the distal end 88 and proximal end (not shown) of the tubular wall 84. The tubular wall 84 has a distal-end region 90 that carries an ablation electrode system 92. In a preferred embodiment, the ablation electrode system 92 includes a plurality of band electrodes 94 and a tip electrode 96. The lumen 86 extends through the tip electrode 92 to allow for placement of the ablation catheter 82 over a guidewire 98. In an alternate configuration the ablation catheter 82 is guided through a sheath. In such a configuration, the need to extend the lumen 86 through the tip electrode 92 is eliminated. The tubular wall 84 includes an orifice 100 positioned within a junction section 102 located between the distal-end region 90 and the proximal-end region 104.

The catheter system 80 further includes an inner mapping catheter 106 configured to fit into and slide within the lumen 86 of the outer ablation catheter 80 and to fit through the orifice 100 contained within the tubular wall 84. The inner mapping catheter 106 includes a tubular wall 108 having a distal-end region 110 that carries a mapping electrode system 112. In a preferred embodiment, the mapping electrode system 112 includes a plurality of band electrodes 114 and a tip electrode 116.

Figures 8, 12:
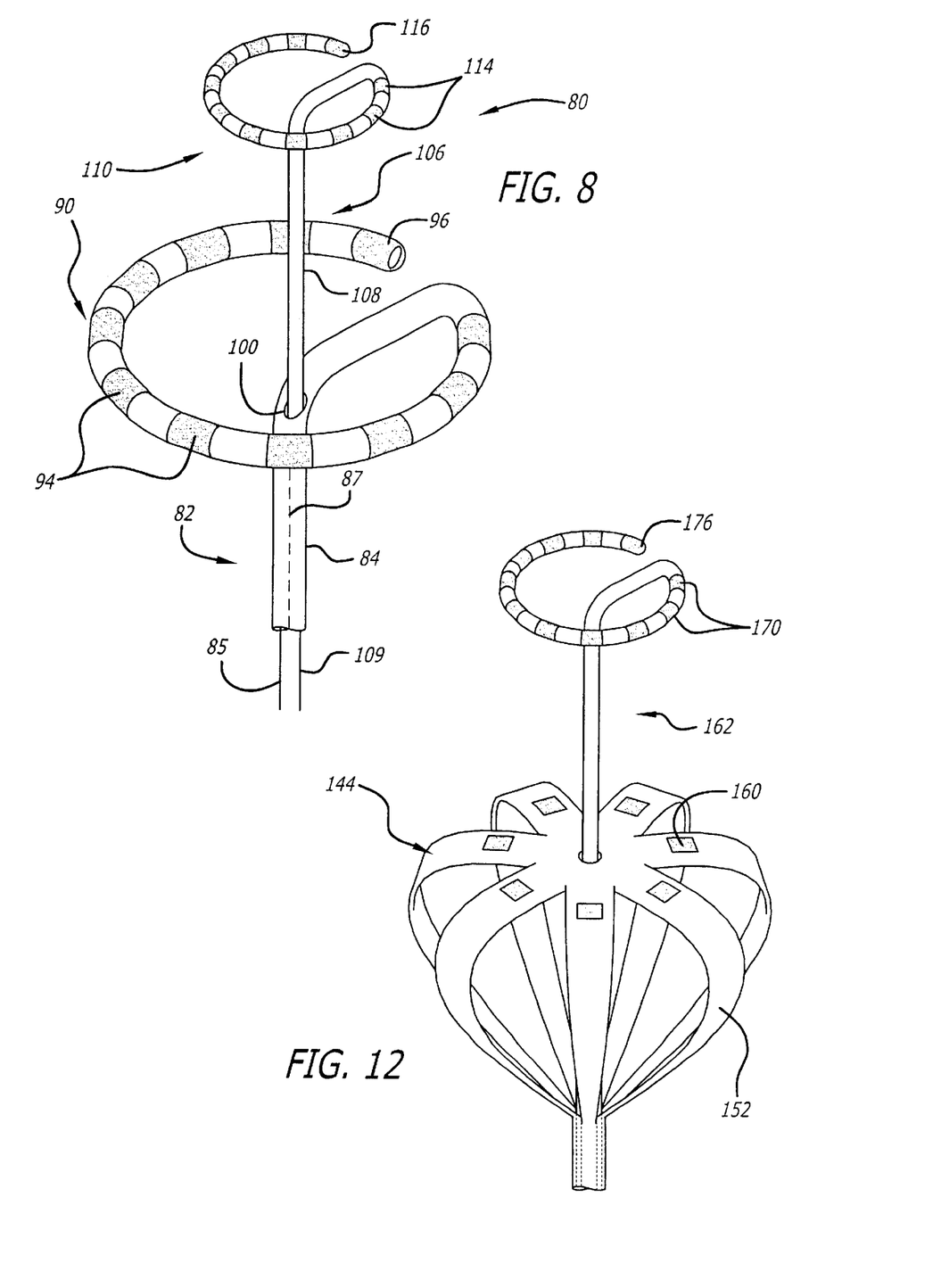
FIG. 8 is an isometric view of the catheter system of FIG. 7 with the distal-end region of the ablation catheter assuming its normally curved shape and the distal-end region of the mapping catheter advanced through the sidewall orifice to assume its normally curved shape.
FIG. 12 is an isometric view of the catheter system of FIG. 11 with the distal-end region of the ablation catheter expanded and the mapping catheter advanced through the lumen to assume its normally curved shape.

As shown in FIG. 8, the distal-end regions 90, 110 of both the ablation catheter 82 and the mapping catheter 106 respectively are formed such that they normally assume an arc shape that nearly forms a complete circle having a radius of curvature. The respective arcs formed in the distal-end regions 90, 110 each lie in a plane substantially parallel to each other. When the distal-end regions 90, 110 assume their normally arced shape, the electrodes 114, 116 carried by the mapping catheter 106 and the electrodes 94, 96 carried by the ablation catheter 82 circumscribe a predefined circle or partial circle. The arc of the ablation catheter 82 is sized to fit around all or part of a vein ostium while the arc of the mapping catheter 110 is sized to fit within the vein. Catheters having different sized arcs may be used depending on the particular anatomy being treated. In one embodiment, the arc shape is provided by shaped-memory nitinol stylets (not shown) carried within the tubular walls 84, 108 of the catheters at the distal-end regions 90, 110. Alternatively, the shaped-memory may be provided by heat-setting the polymer of the catheter.

In an alternate configuration, the tubular walls 84, 108 of the catheters each include a lumen (not shown) that carries a tendon 85, 109. The distal end of the ablation catheter tendon 85 is attached to the distal tip of the tubular wall 84 near the tip electrode 96. Likewise, the distal end of the mapping tendon 109 is attached to the tubular wall 108 near the tip electrode 116. The proximal end of each tendon 85, 109 is attached to a steering mechanism, such as that shown in FIG. 1. Applying tension to the tendons 85, 109 along the length of the catheter shaft causes the radius of curvature of the respective distal-end regions 90, 110 to tighten, i.e., become smaller. Subsequent removal of tension from the tendons 85, 109 allows the distal-end regions 90, 110 to assume their preformed radius of curvature.

Though configured to normally assume their arced shapes, the distal-end regions 90, 110 of both catheters 82, 106 are resiliently deformable and may assume a linear shape when forced to. More specifically, as shown in FIG. 7, the distal-end region 90 of the ablation catheter 82 assumes a linear shape when it is positioned over a guidewire 98. With regard to the mapping catheter 106, its distal-end region 110 assumes a linear shape when it is positioned within the lumen 86 of the ablation catheter 82.

With continued reference to FIG. 7, the junction section 102 positioned between the distal-end region 90 and the proximal-end region 104 of the ablation catheter 82 is formed of a resiliently deformable material, such as Pebax, Nylon or Urethane. The junction section 102 is normally bent to an angle of approximately 90 degrees. When the junction section 102 is in its normally bent form, as shown in FIG. 8, the orifice 100 is positioned such that its center is generally aligned with the axis 87 of the proximal-end region 104 (FIG. 7) of the tubular wall 84. The mapping catheter 106 is similarly configured to include a bend like that of the ablation catheter 82.

In a preferred embodiment, the ablation catheter 82 (FIG. 7) includes a steering mechanism for deflecting the distal-end region 90. In one configuration, the steering mechanism includes an anchor band 118 positioned within the junction section 102, proximal to the orifice 100. The anchor band 118 is secured to the inner surface of the junction section 102 or to a support mechanism (not shown) attached to the distal-end region 90. The steering mechanism further includes a first steering tendon 120 and a second steering tendon 122, each attached at their distal ends to the anchor band 118. The proximal ends of the tendons 120, 122 exit the proximal end of the tubular wall 84 where they are attached to a steering controller similar to that shown in FIG. 1.

Figure 9A:
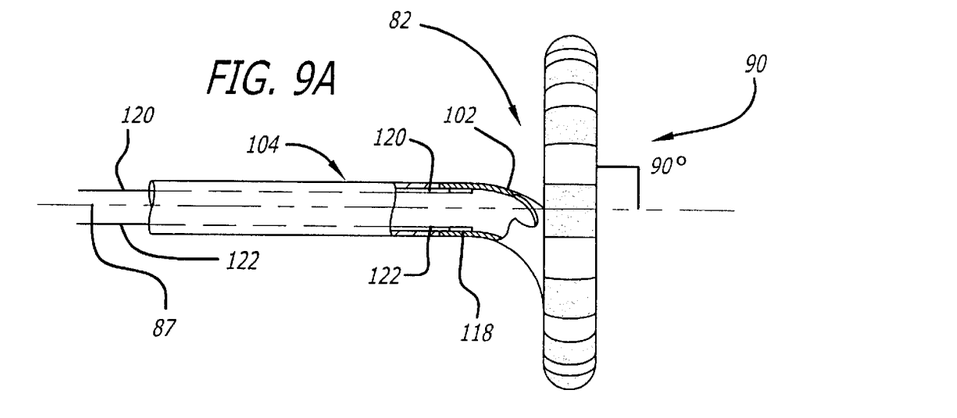
FIG. 9A is a sideview, with partial cutaway of the ablation catheter of FIG. 7 showing the distal-end region in its normally curved state lying in a plane substantially perpendicular to the axis of the proximal-end region of the catheter.
Figure 9B:
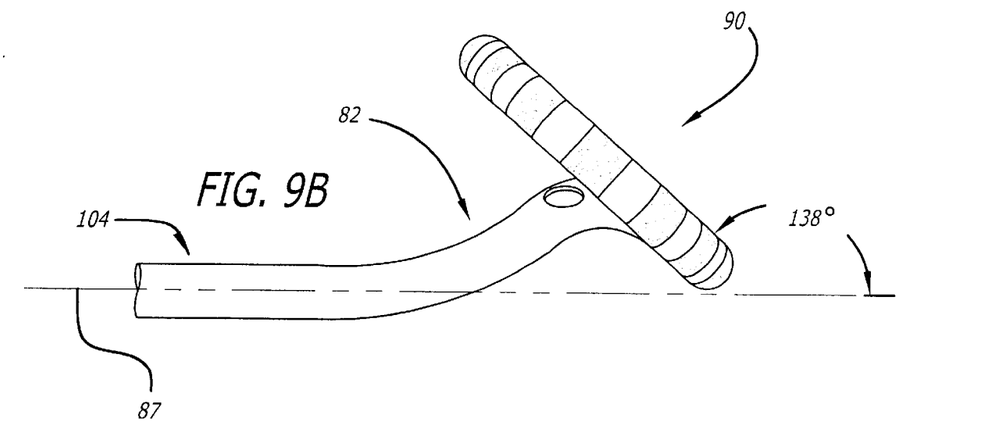
Figure 9C:
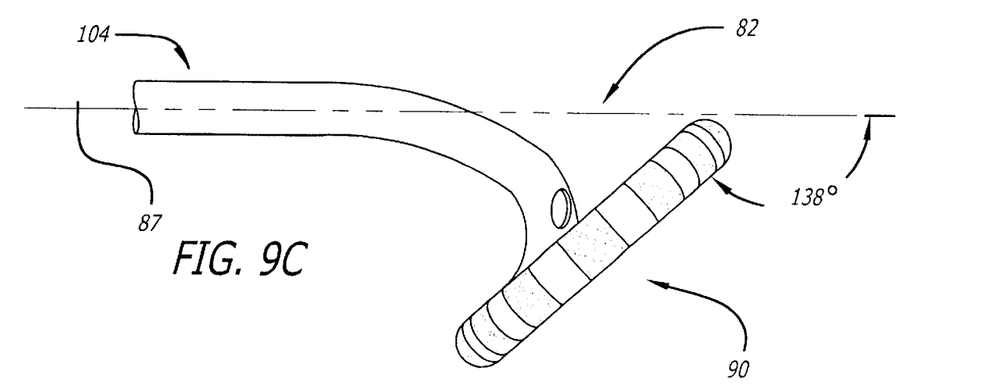

With reference to FIG. 9A, when the steering controller is in a neutral position, i.e., no tension is applied to either tendon 120, 122, the arc formed by the distal-end region 90 of the ablation catheter 82 lies in a plane substantially perpendicular to the axis 87 of the proximal-end region 104. With reference to FIG. 9B, when tension is applied to the first steering tendon 120 (FIG. 9A), the arc formed by the distal-end region 90 of the ablation catheter 82 is deflected in a first direction such that the arc lies in a plane at an angle relative to the axis 87 of the proximal-end region 104. With reference to FIG. 9C, when tension is applied to the second steering tendon 122 (FIG. 9A), the arc formed by the distal-end region 90 of the ablation catheter 82 is deflected in a second direction, opposite the first direction, such that the arc lies in a plane at an angle relative to the axis 87 of the proximal-end region 104.

Figure 10A:
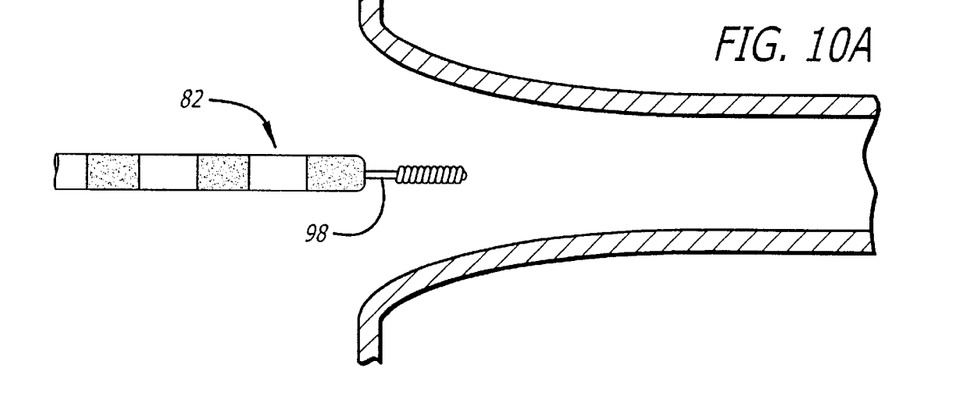
FIG. 10A depicts the catheter system of FIG. 7 deployed near the ostium of a vein with the distal-end region of the ablation catheter straightened by a guidewire.
Figure 10B:
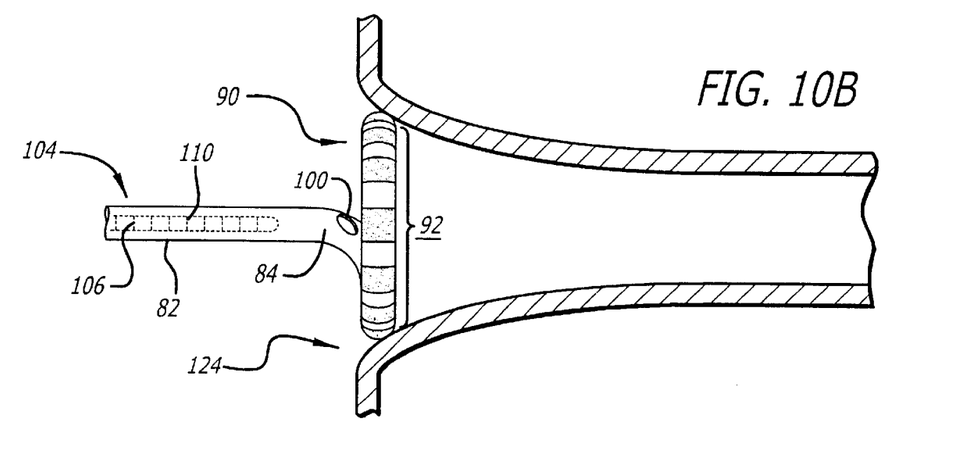
FIG. 10B depicts the catheter system of FIG. 10A with the guidewire removed, the distal-end region of the ablation catheter in its normally curved state and the mapping catheter positioned within the ablation catheter.

With reference to FIG. 10A, in operation, the ablation catheter 82 is introduced into a patient's vascular system and is guided therethrough and into the heart using a guidewire 98. As is meant to be shown in FIG. 10A, the catheter 82 has been advanced into the left atrium of the patient's heart through the septum, and is now directed towards the pulmonary vein that connects to the left atrium of the heart. Alternatively, the ablation catheter 82 may be guided into the heart through a sheath. With reference to FIG. 10B, once the ablation catheter 82 is positioned in the heart, the ablation catheter and guidewire 98 are moved relative each other such that the distal-end region 90 of the ablation catheter 82 is no longer constrained to a straight position by the guidewire and assumes its normally arced shape. The ablation electrode system 92 is then positioned at the ostium 124 of the pulmonary vein. Once the ablation electrode system 92 is positioned, the mapping catheter 106 is guided through the lumen 86 of the ablation catheter 82 toward the orifice 100 in the tubular wall 84. As previously mentioned, the distal-end region 110 of the mapping catheter 106 is formed of a material less rigid than the proximal-end region of ablation catheter 82. As such the normally arced shape of the distal-end region 10 assumes the shape of the proximal-end region 104 of the ablation catheter 82.

Figure 10C:
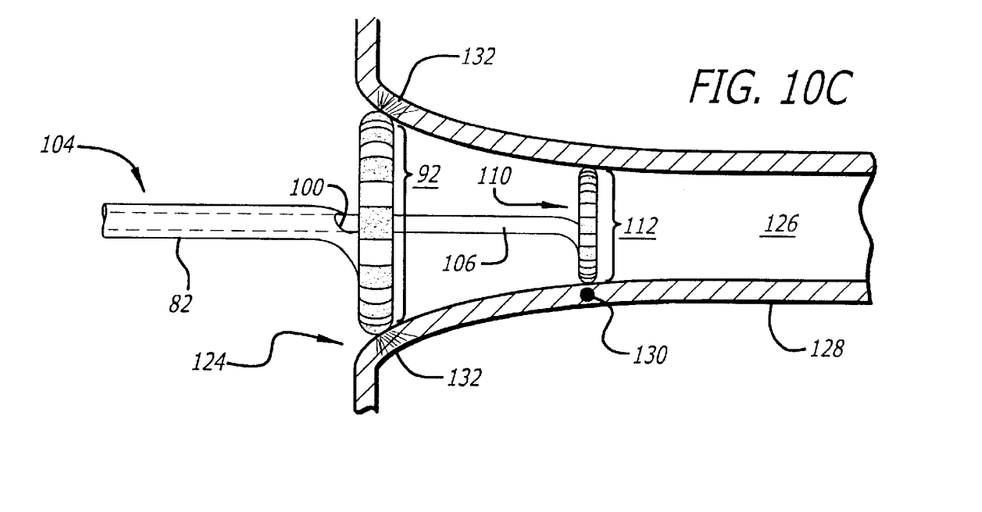
FIG. 10C depicts the catheter system of FIG. 10B with the distal-end region of the mapping catheter extending through the orifice of the ablation catheter and in its normally curved state.

As shown in FIG. 10C, as the distal-end region 110 of the mapping catheter 106 passes through the orifice 100 and is no longer constrained by the proximal-end region 104 of the ablation catheter 82, it assumes its normally arced shape. The distal-end region 110 is advanced into the pulmonary vein 126 until the mapping electrode system 112 contacts the tissue 128. Electrical signals, i.e., pulmonary vein potentials, are sensed by the mapping electrode system 112 and sent to the mapping processor where they are analyzed to determine if the pulmonary vein contains an arrthymogenic origin for atrial arrhythmia.

If it is determined that the pulmonary vein contains an arrthymogenic origin 130, the ablation electrode system 92 is positioned such that it circumferentially engages the tissue around the pulmonary vein ostium 124. Energy is then applied to the ablation electrode system 92 to ablate the tissue around the ostium 124 to thereby form a circumferential lesion 132 which blocks electrical conduction from the arrthymogenic origin 130 along the pulmonary vein 126 wall into the left atrium. To ensure the formation of a continuous circumferential lesion 132, energy may be applied to the ablation electrode system 92 using a combination unipolar/bipolar technique and/or phasing technique such as that described in U.S. Pat. Nos. 6,050,994, 6,059,778 and 6,171,305, the disclosures of which are hereby incorporated by reference.

With reference to FIG. 8, in a preferred embodiment of the catheter system 80 the distal-end region 110 of the mapping catheter 106 and the distal-end region 90 of the ablation catheter 82 may be positioned relative each other such that the mapping electrodes 114, 116 align with the ablation electrodes 94, 96. Specifically, the catheter mapping electrodes may be positioned such that the tip electrode 116 aligns with the ablation tip electrode 96, the mapping band electrode 114 adjacent the mapping tip electrode aligns with the ablation band electrode 94 adjacent the ablation tip electrode and so on. Alignment of the electrodes 94, 96, 114, 116 may be accomplished using a marker visible under fluoroscopy located on the shafts of the catheter. Using a marker allows for the mapping catheter 106 and the ablation catheter 82 to rotate relative each other.

Alternatively, alignment of the electrodes 94, 96, 114, 116 may be accomplished by a guide system carried by the catheter system. The guide system may include a linear groove (not shown) along the interior of the proximal-end region 104 of the ablation catheter 82 and a complimentary linear protrusion (not shown) along the exterior of the proximal-end region of the mapping catheter 106. During deployment of the mapping catheter 106 through the ablation catheter 82, the protrusion is positioned within the groove to align the catheter such that their respective electrodes are aligned. Alternatively, the groove may be carried by the mapping catheter 106 and the protrusion by the ablation catheter 82. In this case, the catheters 82 and 106 are not free to rotate relative to each other.

Figure 11:
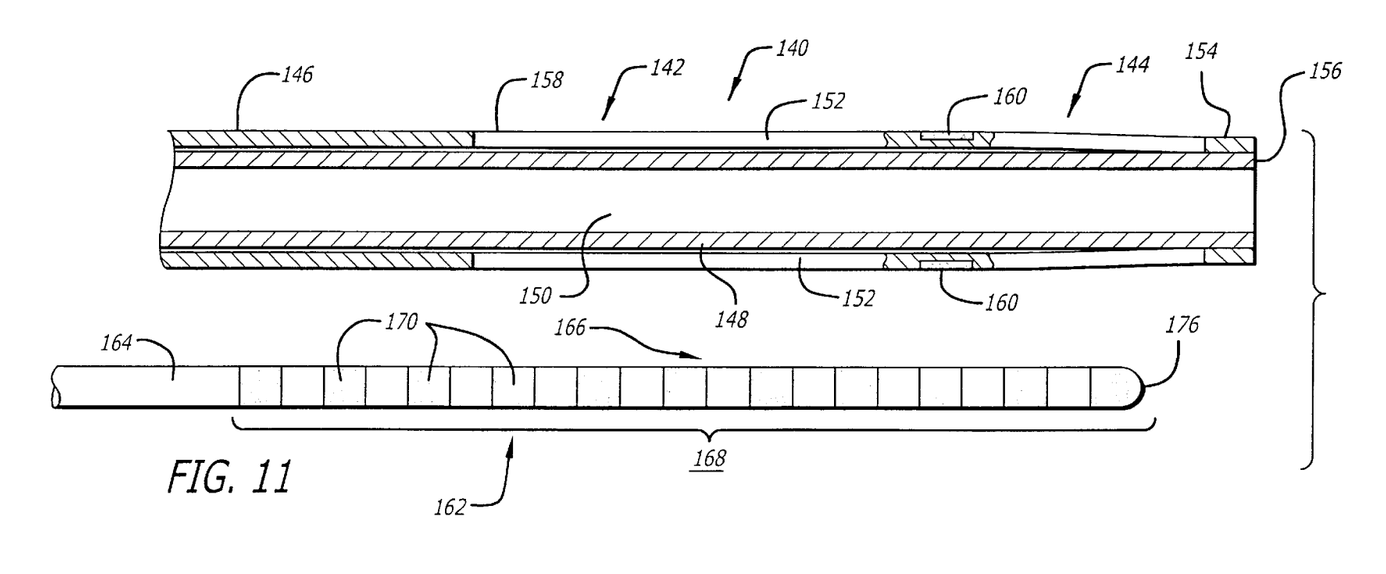
FIG. 11 is a cross-sectional side view of a catheter system configured in accordance with another embodiment of the invention including an open-lumen ablation catheter having an expandable distal-end region (shown collapsed) and a mapping catheter sized to fit within the ablation catheter and having a normally curved distal-end region (shown straightened)

With reference to FIG. 11, in another embodiment of the invention, a catheter system 140 includes an outer ablation catheter 142 having an expandable ablation electrode system 144. The ablation catheter 142 includes an outer tubular member 146 and an inner tubular member 148 slidably disposed within the outer tubular member. The inner tubular member 148 defines an outer-catheter lumen 150. The outer ablation catheter 142 further includes a plurality of outwardly bendable segments 152 that, in this embodiment, take the form of elongated strips. Each segment 152 is secured at its distal end 154 to the distal end 156 of the inner tubular member 148 and at its proximal end 158 to the outer tubular member 146 at a point proximal the attachment points of the distal ends. Configured as such, movement of the inner tubular member 148 in the proximal direction relative the outer tubular member 146 causes the segments 152 to bend outward, as shown in FIG. 12. The width of the strips 152 depends on the number required to be placed about the catheter. The more strips that are required, the narrower each one may be. However, there may be a maximum width regardless of how few strips exist. Further, the strips may not be "elongated" but may be shorter in length depending on the radius desired to be obtained when the strips are bent outward.

An ablation electrode 160 is located on each of the segments 152. Lead wires (not shown) run the length of the ablation catheter 142 and connect the ablation electrodes 160 to an energy generator/processor such as that shown in FIG. 1. The lead wires are carried by a lumen (not shown) contained within the outer tubular member 146 and the bendable segments 152.

The catheter system 140 further includes an inner mapping catheter 162 configured to fit and slide within the outer-catheter lumen 150. The inner mapping catheter 162 includes a tubular wall 164 having a distal-end region 166 that carries a mapping electrode system 168. In a preferred embodiment, the mapping electrode system 168 includes a plurality of band electrodes 170 and a tip electrode 176. The distal-end region 166 of the tubular wall 164 has shaped-memory properties and is formed to normally assume an arc shape that nearly forms a complete circle as shown in FIG. 12. The distal-end region 166 of the mapping catheter 162 is less rigid than the inner tubular member 148 of the ablation catheter 142 and assumes the shape of the inner tubular member when it is positioned therein. The configuration of the mapping catheter 162 is similar to that of FIG. 7.

Figure 13A:
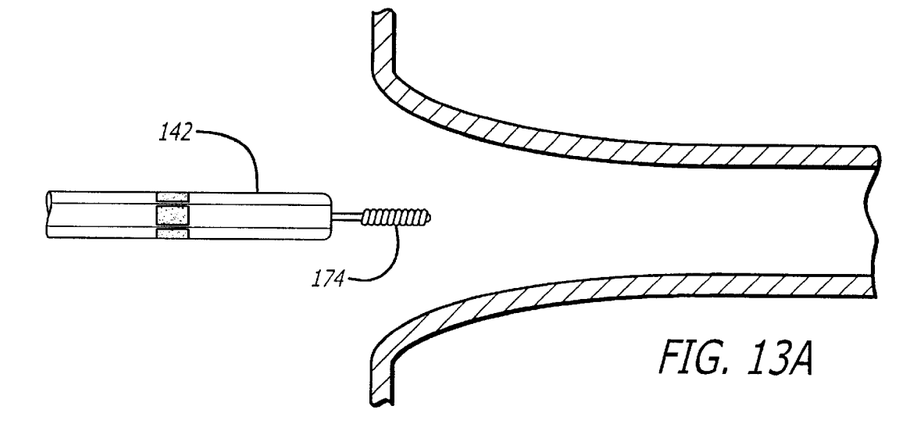
FIG. 13A depicts the catheter system of FIG. 11 being deployed near the ostium of a vein with the ablation catheter being guided over a guidewire.
Figure 13B:
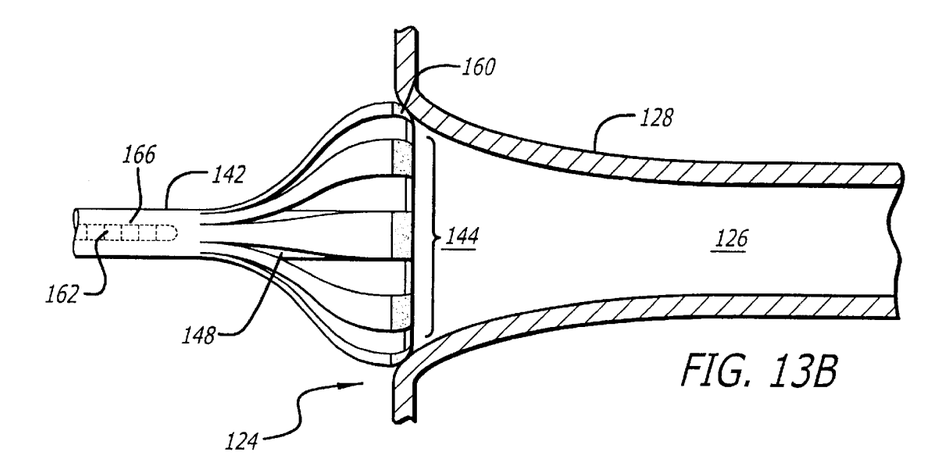
FIG. 13B depicts the catheter system of FIG. 13A with the guidewire removed, the distal-end region of the ablation catheter expanded and the mapping catheter positioned within the ablation catheter.

With reference to FIG. 13A, in operation, the ablation catheter 142 is introduced into a patient's vascular system and is guided therethrough and into the heart using a guidewire 174. Alternatively, the ablation catheter 142 may be guided into the heart through a sheath. Once the ablation catheter 142 is positioned in the heart, the guidewire 174 is removed and the inner tube 148 (FIG. 11) of the ablation catheter 142 is retracted relative to the outer tube 146, thereby causing the ablation electrode system 144 to assume its expanded form as shown in FIG. 13B. The ablation electrode system 144 is then positioned at the ostium 124 of the pulmonary vein 126, such that the ablation electrodes 160 contact the tissue 128.

Once the ablation electrode system 144 is positioned at the pulmonary vein ostium, the mapping catheter 162 is guided through the lumen 150 (FIG. 11) of the ablation catheter 142. As previously mentioned, the mapping catheter 162 is formed of a material less rigid than the inner tubular member 148 of the ablation catheter 142, as such the normally arced shape of the distal-end region assumes the shape of the inner tubular member 148.

Figure 13C:
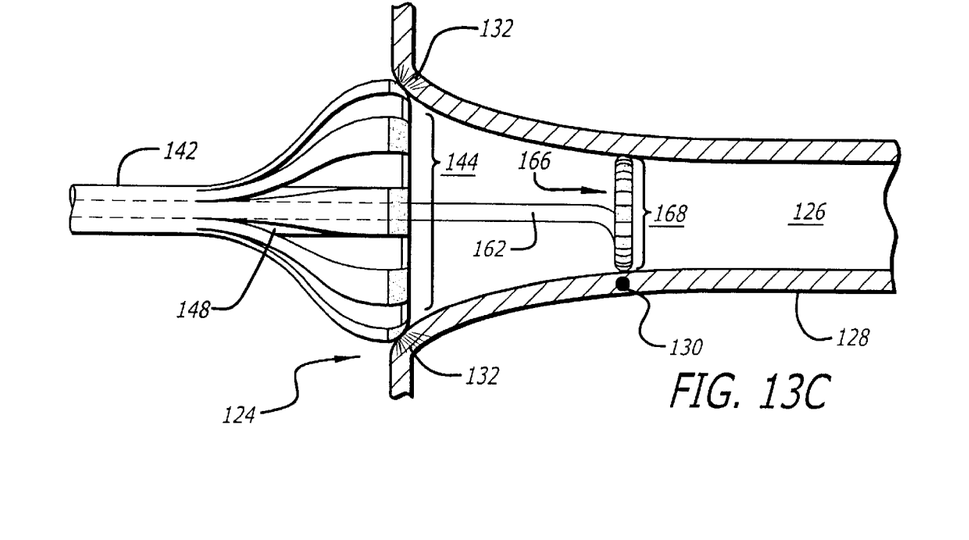
FIG. 13C depicts the catheter system of FIG. 13B with the distal-end region of the mapping catheter extending through the top of the ablation catheter to assume its normally curved shape.

As shown in FIG. 13C, as the distal-end region 166 of the mapping catheter 162 passes through the top of the inner tubular member 148, it assumes its normally curved shape. The distal-end region 166 is advanced into the pulmonary vein until the mapping electrode system 168 contacts the tissue 128. Electrical signals are sensed by the mapping electrode system 168 and sent to a mapping processor where they are analyzed to determine if the pulmonary vein contains an arrthymogenic origin for atrial arrhythmia.

If it is determined that the pulmonary vein contains an arrthymogenic origin 130, the ablation electrode system 144 is positioned to ensure that it circumferentially engages the tissue around the pulmonary vein ostium 124. Energy is then applied to the ablation electrode system 144 to ablate the tissue around the ostium 124 to thereby form a circumferential lesion 132 which blocks electrical conduction from the arrthymogenic origin 130 along the longitudinal axis of the pulmonary vein 126 wall into the left atrium. To ensure the formation of a continuous circumferential lesion 132, energy may be applied to the ablation electrode system 144 using a combination unipolar/bipolar technique and/or phasing technique such as those described in U.S. Pat. Nos. 6,050,994, 6,059,778 and 6,171,305, the disclosures of which are hereby incorporated by reference.

Figure 14:
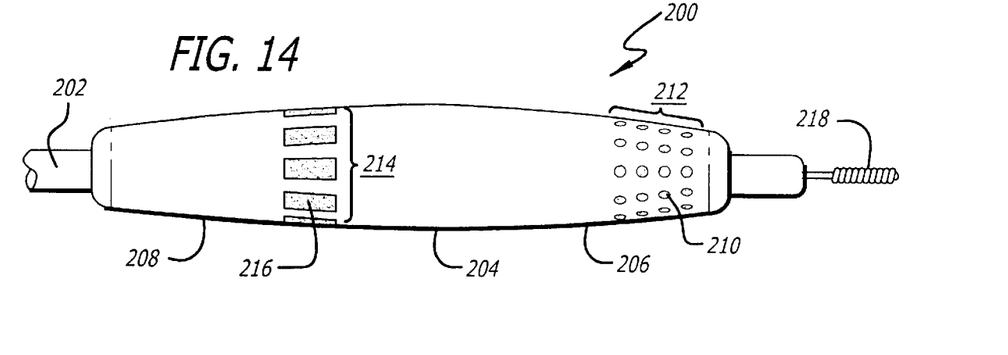
FIG. 14 depicts a catheter system configured in accordance with another embodiment of the invention having an expandable member (shown collapsed) carrying a mapping electrode system at its distal end and an ablation electrode system near its proximal end.

With reference to FIG. 14, in another embodiment of the invention, a catheter system 200 includes a catheter shaft 202 having a radially expandable member 204 at its distal end. In one configuration, the expandable member 204 comprises an inflatable balloon having a distal-end region 206 and a proximal-end region 208. The balloon 204 is configured such that when it is inflated, the outside diameter of the distal-end region 206 is less than the outside diameter of the proximal-end region 208. A plurality of mapping electrodes 210 arranged in an array at the distal end of the balloon 204 form a mapping electrode system 212. The mapping electrodes 210 may comprise a metallic material deposited on the outer surface of the balloon using known techniques, such as but not limited to plasma depositing, sputter coating or chemical vapor deposition. An ablation electrode system 214 is positioned at the proximal-end region 208 of the balloon 204. The ablation electrode system 214 may comprise one or more ablation electrodes 216 arranged to form a circumferential band around the balloon 204. The ablation electrodes 216 may comprise a metallic material deposited on the outer surface of the balloon 204.

The catheter shaft 202 includes a lumen that allows for deployment of the catheter system 200 over a guide wire 218. Alternatively, the catheter system 200 may be deployed through a guiding sheath.

Figure 15:
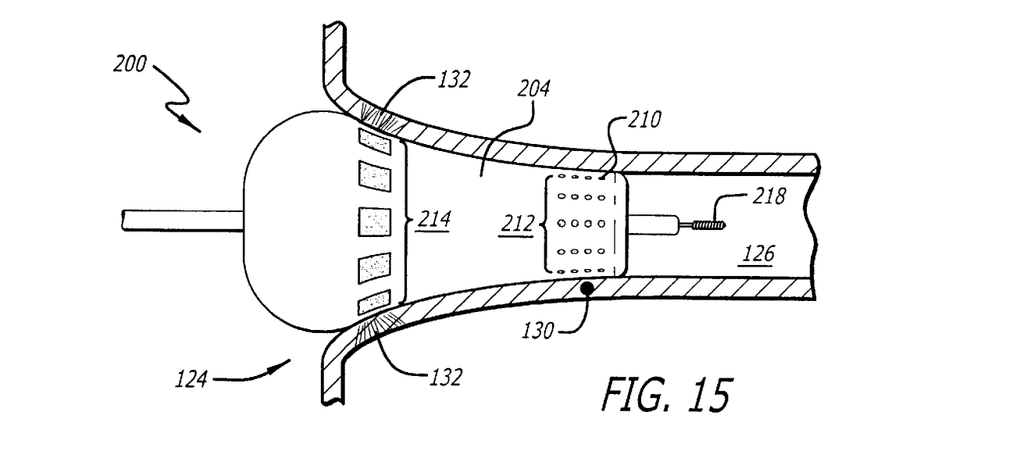
FIG. 15 depicts the catheter of FIG. 14 with the radially expandable member expanded and deployed within a vein.

With reference to FIG. 15, in operation, the distal end of the catheter system 200 is guided by a guide wire 218 to the interior of the pulmonary vein 126. Once properly positioned, the balloon 204 is inflated to a level sufficient to force contact between the mapping electrode system 212 and the circumferential wall of the vein 126. The mapping electrodes 210 sense pulmonary vein potentials throughout the circumference and depth of the pulmonary vein 126 and pass them to a mapping processor to determine if the pulmonary vein contains an arrthymogenic origin for atrial arrhythmia.

If it is determined that the pulmonary vein contains an arrthymogenic origin 130, the balloon is further inflated to force contact between the ablation electrode system 214 and the tissue around the pulmonary vein ostium 124. Energy is then applied to the ablation electrode system 214 to ablate the tissue around the ostium 124 to thereby form a circumferential lesion 132 which blocks electrical conduction from the arrthymogenic origin 130 along the longitudinal axis of the pulmonary vein 126 wall into the left atrium. To ensure the formation of a continuous circumferential lesion 132, energy may be applied to the ablation electrode system 214 using a combination unipolar/bipolar technique and/or phasing technique such as that described in U.S. Pat. Nos. 6,050,994, 6,059,778 and 6,171,305, the disclosures of which are hereby incorporated by reference.

In the configuration thus described, a single balloon is used to deploy both the mapping electrode system and the ablation electrode system. In alternate configurations (not shown) of this embodiment, the catheter system employ multiple balloons. A first balloon deploys the mapping electrode system while a second balloon deploys the ablation electrode system.

Figure 16:
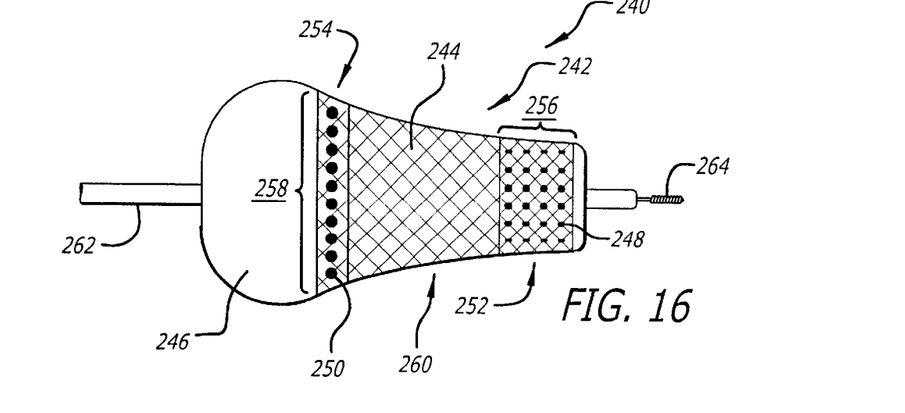
FIG. 16 depicts a catheter system configured in accordance with another embodiment of the invention having a radially expandable member (shown expanded) and carrying a framework having a mapping electrode system at its distal end and an ablation electrode system near its proximal end.

With reference to FIG. 16, in another embodiment of the catheter system 240, the expandable member 242 comprises a matrix framework 244 or mesh positioned on an inflatable device 246, such as a balloon. The framework 244 is secured to the balloon 246 through known adhesive bonding techniques and is expanded by inflation of the balloon. The construction of the framework 244 determines the size of its expansion. Specifically, a more "loose" framework 244 allows for greater expansion. Mapping electrodes 248 and ablation electrodes 250 are mounted on the framework 244 at the distal-end region 252 and the proximal-end region 254, respectively to define a mapping electrode system 256 and an ablation electrode system 258. The ablation electrodes 250 are positioned adjacent each other in a single row around the balloon 246 to form a circumferential electrode band. By using only a single row of electrodes 250, a narrow ablation band is provided, as such, the ablation site is localized and the risk of pulmonary vein stenosis is minimized. In alternative configurations, more rows of ablation electrodes 250 may be added to increase the width of the ablation band circumference. The mapping electrodes 248 and ablation electrodes 250 are isolated from each other by insulating coatings on the balloon 246 and/or on the framework 244.

In one configuration, the framework 244 includes metallic and non-metallic portions. A first metallic portion contains the mapping electrodes 248 while a second metallic portion contains the ablation electrodes 250. Conductive wires carried by the metallic portions serve as lead wires between the electrodes 248, 250 and the catheter shaft 262. The lead wires are carried within the wall of the expandable member 242 and into the catheter shaft 262. For a configuration deployed using a guidewire 264, the lead wires are carried by the wall of the catheter shaft 262 to the proximal end of the catheter. The metallic portions are separated by a non-metallic portion 260. In a preferred embodiment, the non-metallic portion is formed from PTFE or other non-thrombogenic material.

In alternate configurations, deployment of the framework could be through the use of mechanical means such as a spring tension or a deployment tendon/wire to expand and contract the framework.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter system for use during electrophysiological procedures on biological tissue, said catheter system comprising:
an outer catheter having a lumen therethrough and a distal-end region carrying a first electrode system a first orifice at a distal end of the electrode system and a second orifice located adjacent a proximal end of the first electrode system, the lumen extending through the portion of the distal-end region carrying the first electrode system; and
an inner catheter sized to fit within the lumen and to slide therein and pass through the second orifice, the inner catheter having a distal-end region carrying a second electrode system.

2. The catheter system of claim 1 wherein the first electrode system comprises a plurality of band electrodes positioned along the length of the distal-end region.

3. The catheter system of claim 1 wherein the second electrode system comprises a plurality of band electrodes positioned along the length of the distal-end region.

4. The catheter system of claim 1 wherein the outer catheter further comprises a tendon having a distal end attached to the distal-end region of the outer catheter and a proximal end exiting a proximal end of the outer catheter, wherein movement of the tendon along the length of the outer catheter causes the distal-end region of the cater catheter to curve.

5. The catheter system of claim 1 wherein the outer catheter is configured to have a preshaped curve at its distal-end region.

6. The catheter system of claim 5 wherein the preshaped curve is imparted by a shaped-memory stylet carried by the distal-end region of the outer catheter.

7. The catheter system of claim 5 wherein the preshaped curve is generally circular.

8. The catheter system of claim 5 wherein the preshaped curve has a radius of curvature and the outer catheter further comprises a tendon having a distal end attached to the distal-end region of the outer catheter and a proximal end exiting a proximal end of the outer catheter, wherein movement of the tendon along the length of the outer catheter decreases the radius of curvature.

9. The catheter system of claim 1 wherein the inner catheter further comprises a tendon having a distal end attached to the distal-end region of the inner catheter and a proximal end exiting a proximal end of the inner catheter, wherein movement of the tendon along the length of the outer catheter causes the distal-end region of the inner catheter to curve.

10. The catheter system of claim 1 wherein the inner catheter is configured to have a preshaped curve at its distal-end region.

11. The catheter system of claim 10 wherein the preshaped curve is imparted by a shaped-memory stylet carried by the distal-cud region of the inner catheter.

12. The catheter system of claim 10 wherein the preshaped carve is generally circular.

13. The catheter system of claim 10 wherein the preshaped curve has a radius of curvature and the inner catheter further comprises a tendon having a distal end attached to the distal-end region of the inner catheter and a proximal end exiting a proximal end of the inner catheter, wherein movement of the tendon along the length of the inner catheter decreases the radius of curvature.

14. The catheter system of claim 1 further comprising:
a generator adapted to provide energy to the first electrode system; and
a processor adapted to receive electrical signals from the second electrode system, the signals indicative of electrical activity in the tissue.

15. The catheter system of claim 1 further comprising:
a generator adapted to provide energy to the second-electrode system; and
a processor adapted to receive electrical signals from the first electrode system, the signals indicative of electrical activity in the tissue.

16. A catheter system for use during electrophysiological procedures on biological tissue, said catheter system comprising:
an outer catheter having a tubular wall that defines a lumen that terminates in a tip orifice, the outer catheter also having a distal-end region carrying a first electrode system, a proximal-end region, and a sidewall orifice formed in the tubular wall adjacent a proximal end of the first electrode system; and
an inner catheter sized to fit within the lumen and to slide therein and to fit through the sidewall orifice, the inner catheter having a distal-end region carrying a second electrode system.

17. The catheter system of claim 16 wherein the tubular wall comprises a resiliently deformable junction section between the distal-end region and the proximal end region, the junction section having a normally bent form that generally aligns the center of the sidewall orifice with the axis of the proximal-end region of the outer catheter.

18. The catheter of claim 17 wherein the normally bent form comprises an approximate 90 degree bend.

19. The catheter system of claim 17 wherein the outer catheter further comprises a tendon having a distal end attached proximate the inner wall of the tubular wall and a proximal end exiting a proximal end of the outer catheter wall, wherein movement of the tendon along the length of the tubular wall causes the distal-end region to deflect about the junction section relative to the proximal-end region.

20. The catheter system of claim 16 wherein the outer catheter comprises a shape-memory stylet for imparting a preshaped curve to the distal-end region of the outer catheter.

21. The catheter system of claim 16 wherein the inner catheter comprises a shape-memory stylet for imparting a preshaped curve in the distal-end region of the inner catheter.

22. The catheter system of claim 16 wherein
the outer catheter comprises a shape memory stylet for imparting a generally circular curve to the distal-end region of the outer catheter the curve lying substantially within a first plane; and
the inner catheter comprises a shape-memory stylet tar imparting a generally circular curve to the distal-end region or the inner catheter, the curve lying substantially within a second plane, the second plane being substantially parallel to the first plane.

23. The catheter system of claim 22 wherein the first electrode system and the second electrode system each comprise a plurality of kind electrodes positioned along the length of the their respective distal-end region and the catheter system further comprises an alignment system adapted to align the curved distal-end region of the inner catheter with the curved distal-end region of the outer catheter such that the hand electrodes of the respective catheters are aligned with each other.

24. The catheter system of claim 23 wherein the alignment system comprises a pair of markers, each visible under fluoroscopy one marker carried on a proximal region of the inner catheter and the other marker carried on the proximal region of the outer catheter.

25. The catheter system of claim 23 wherein the alignment system comprises a grove along an outer surface of a proximal region of the inner catheter and a complimentary protrusion along an inner surface of the outer catheter.

26. The catheter system of claim 23 wherein the alignment system comprises a protrusion along an outer surface of a proximal region of the inner catheter and a complementary groove along an inner surface of the outer catheter.

27. The catheter system of claim 16 wherein the first electrode system comprises a plurality of band electrodes positioned along the length of the distal-end region.

28. The catheter system of claim 16 wherein the second electrode system comprises a plurality of band electrodes positioned along the length of the distal-end region.

29. The catheter system of claim 16 further comprising:
a generator adapted to provide energy to the first electrode system; and
a processor adapted to receive electrical signals from the second electrode system, the signals indicative of electrical activity in the tissue.

* * * * *

UNITED STATES PATENT AND TRADEMARK OFFICE
CERTIFICATE OF CORRECTION

PATENT NO. : 6,771,996 B2
DATED : August 3, 2004
INVENTOR(S) : Wade A. Bowe and Jeffrey A. Hall It is certified that error appears in the above-identified patent and that said Letters Patent is hereby corrected as shown below:

Column 12,
Line 28, delete "10" and insert -- 110 --.

Column 16,
Line 19, delete "therethrough and" and insert -- therethrough, --.
Line 20, delete "system" and insert -- system, --.
Line 26, delete "lumen and" and insert -- lumen, --.
Line 41, delete "cater" and insert -- outer --.

Column 17,
Line 3, delete "distal-cud" and insert -- distal-end --.
Line 4, delete "carve" and insert -- curve --.
Line 51, delete "catheter wall," and insert -- catheter, --.

Column 18,
Line 12, delete "catheter" and insert -- catheter, --.
Line 14, delete "tar" and insert -- for --.
Line 16, delete "or" and insert -- of --.
Line 21, delete "kind" and insert -- band --.
Line 26, delete "hand" and insert -- band --.
Line 34, delete "grove" and insert -- groove --.
Line 35, delete "complimentary" and insert -- complementary --.

Signed and Sealed this

Twenty-eighth Day of June, 2005

JON W. DUDAS
*Director of the United States Patent and Trademark Office*